US010527594B2

(12) United States Patent
Sezaki et al.

(10) Patent No.: US 10,527,594 B2
(45) Date of Patent: Jan. 7, 2020

(54) LIQUID CHROMATOGRAPHY MEASUREMENT METHOD, LIQUID CHROMATOGRAPHY MEASUREMENT INSTRUMENT, AND LIQUID CHROMATOGRAPHY MEASUREMENT PROGRAM STORAGE MEDIUM

(71) Applicant: ARKRAY, Inc., Kyoto (JP)

(72) Inventors: Akira Sezaki, Kyoto (JP); Takeshi Takagi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 304 days.

(21) Appl. No.: 15/490,320

(22) Filed: Apr. 18, 2017

(65) Prior Publication Data
US 2017/0307571 A1   Oct. 26, 2017

(30) Foreign Application Priority Data

Apr. 20, 2016 (JP) ................................. 2016-084718
Apr. 10, 2017 (JP) ................................. 2017-077851

(51) Int. Cl.
*G01N 30/38* (2006.01)
*G01N 30/86* (2006.01)
(Continued)

(52) U.S. Cl.
CPC ......... *G01N 30/38* (2013.01); *G01N 30/8665* (2013.01); *G01N 33/491* (2013.01); *G01N 2030/027* (2013.01)

(58) Field of Classification Search
CPC .... G01N 30/38; G01N 30/8665; G01N 30/34; G01N 30/88; G01N 33/491;
(Continued)

(56) References Cited

U.S. PATENT DOCUMENTS 5,294,336 A * 3/1994 Mizuno ................. B01D 15/08
                                                          210/143
5,417,853 A * 5/1995 Mizuno ................. G01N 30/88
                                                          210/143
(Continued)

FOREIGN PATENT DOCUMENTS

EP    1103812 A1    5/2001
EP    2012111 A1    1/2009
(Continued)

OTHER PUBLICATIONS

The extended European search report issued by the European Patent Office dated Jul. 17, 2017, which corresponds to European Patent Application No. 17167119.1-1554 and is related to U.S. Appl. No. 15/490,320; 14pp.

(Continued)

*Primary Examiner* — Nimeshkumar D Patel
*Assistant Examiner* — Gedeon M Kidanu
(74) *Attorney, Agent, or Firm* — Studebaker & Brackett PC

(57) ABSTRACT

A liquid chromatography measurement method includes: switching between a first measurement mode using a liquid chromatography method in which hemoglobin A1c and a hemoglobin variant are measured in a measurement sample by sequentially delivering a first component-separating eluent, a second component-separating eluent and a wash eluent to an analytical column, and a second measurement mode using the liquid chromatography method in which the hemoglobin A1c is measured by sequentially delivering the first component-separating eluent and the wash eluent to the analytical column; delivering the wash eluent in the first measurement mode prior to an influence from the second component-separating eluent disappearing such that a first retention time of the hemoglobin A1c in the first measurement mode and a second retention time of the hemoglobin (Continued)

A1c in the second measurement mode are substantially the same as each other; and delivering the first component-separating eluent after the wash eluent.

7 Claims, 7 Drawing Sheets

(51) Int. Cl.
*G01N 33/49* (2006.01)
*G01N 30/02* (2006.01)
(58) Field of Classification Search
CPC ....... G01N 30/8668; G01N 2030/8822; G01N 2030/027
See application file for complete search history.

(56) References Cited

U.S. PATENT DOCUMENTS

| | | | | |
|---|---|---|---|---|
| 5,543,315 | A * | 8/1996 | Sugiyama | G01N 30/28 210/198.2 |
| 5,804,142 | A * | 9/1998 | Ito | G01N 30/88 210/198.2 |
| 5,843,788 | A * | 12/1998 | Rexroad, Jr. | G01N 30/88 436/161 |
| 6,428,704 | B1 * | 8/2002 | Setoguchi | G01N 30/96 210/198.2 |
| 6,488,857 | B1 * | 12/2002 | Shimada | B01D 15/362 210/198.2 |
| 8,268,625 | B2 * | 9/2012 | Sugiyama | G01N 21/31 356/432 |
| 2009/0317912 | A1 * | 12/2009 | Sugiyama | G01N 21/314 436/67 |
| 2010/0291691 | A1 * | 11/2010 | Sugiyama | G01N 21/31 436/67 |
| 2011/0186511 | A1 * | 8/2011 | Sakai | G01N 30/24 210/635 |
| 2012/0017706 | A1 * | 1/2012 | Yoshida | G01N 30/8651 73/866.3 |
| 2013/0199277 | A1 * | 8/2013 | Taira | G01N 30/88 73/61.52 |
| 2014/0238113 | A1 * | 8/2014 | Oishi | G01N 30/32 73/61.56 |
| 2015/0377846 | A1 * | 12/2015 | Ishikawa | G01N 30/88 73/61.41 |

FOREIGN PATENT DOCUMENTS

| | | |
|---|---|---|
| JP | H10-10107 A | 1/1998 |
| JP | 2009-236768 A | 10/2009 |
| WO | 97/41771 A1 | 11/1997 |

OTHER PUBLICATIONS

Bio-Rad Laboratories, Inc.; VARIANT™ II Dual Program; Fully Automated HbA2, HbF and HbA1c Determination; 2 pages.
An Office Action mailed by the European Patent Office dated Apr. 17, 2019, which corresponds to European Patent Application No. 17167119.1-1020 and is related to U.S. Appl. No. 15/490,320.

* cited by examiner

LIQUID CHROMATOGRAPHY MEASUREMENT METHOD, LIQUID CHROMATOGRAPHY MEASUREMENT INSTRUMENT, AND LIQUID CHROMATOGRAPHY MEASUREMENT PROGRAM STORAGE MEDIUM

CROSS-REFERENCE TO RELATED APPLICATIONS

This application is based on and claims priority under 35 USC 119 from Japanese Patent Applications No. 2016-084718 filed on Apr. 20, 2016, and No. 2017-077851 filed on Apr. 10, 2017, the disclosures of which are incorporated by reference herein.

BACKGROUND

Technical Field

The present disclosure relates to a liquid chromatography measurement method, a liquid chromatography measurement instrument, a liquid chromatography measurement program, and a storage medium. The present disclosure in particular relates to a liquid chromatography measurement method, a liquid chromatography measurement instrument, a liquid chromatography measurement program, and a storage medium that are used to analyze biological samples such as blood.

Related Art

Hitherto, a method has been proposed of using a liquid chromatography method to measure, for example, glycated hemoglobin (HbA1c) and Hb variants in a measurement sample such as blood (for example, see Japanese Patent Application Laid-Open (JP-A) No. 2009-236768) and the "Variant™ II Dual Program" catalog by Bio-Rad Laboratories, Inc.

Hitherto, in order to measure glycated hemoglobin (HbA1c) in a measurement sample, normally, either separate measurement instruments are used or analytical columns are swapped for: measurements to detect a hemoglobin variant and to separate or remove the hemoglobin variant to measure both the HbA1c and the hemoglobin variant (in variant mode); and measurements to primarily measure hemoglobin A1c (in fast mode). In particular, this is because different eluents need to be used for taking measurements in various cases since conditions such as eluent concentration in the lines have an influence on measurement accuracy. Thus, hitherto, in liquid chromatography instruments, even for instruments capable of measuring in a fast mode and a variant mode, in order to change the measurement mode, a washing process and an equilibrating process have been necessary for the column and inside the lines. More specifically, in order to change the measurement mode, the column and inside the lines are washed as an end sequence when finishing a measurement mode, and only then is the measurement mode changed. Then, in the post-change measurement mode, a start sequence is implemented to achieve an equilibrated state of the column and inside the lines. Switching between plural measurement modes for plural measurement samples and then performing measurements on the measurements samples successively without the addition of an extra process has not yet been performed hitherto.

As described above, in order to change the measurement mode, due to the need for a wash process and an equilibrating process for the column and inside the lines, a lot of eluent is used and the duration of measurement is also a long duration. Further, when switching between the variant mode and the fast mode for plural measurement samples to perform successive measurements with a single liquid chromatography instrument, the present inventors have found an issue in that sometimes an eluent used only in the variant mode has an influence on the next measurement, and sometimes an offset arises in the retention time of HbA1c. This issue is not such a significant issue when executing primarily only one of the variant mode and the fast mode in a single liquid chromatography instrument.

However, in cases in which there is switching between the two measurement modes and successive execution with a single liquid chromatography instrument, if an offset occurs in retention time of the measured HbA1c, there is an issue of confusion arising when a user is identifying the peak for HbA1c based on a retention time for HbA1c, complicating the process to identify the HbA1c peak in the liquid chromatography instrument. Thus, when executing a switch between the two measurement modes in a single liquid chromatography instrument, there has been a need to provide enough time for switching, and it has been difficult to shorten the measurement time.

SUMMARY

The present disclosure provides a liquid chromatography measurement method, a liquid chromatography measurement instrument, a liquid chromatography measurement program, and a storage medium that are capable of shortening measurement time while suppressing offset from occurring in the retention time of HbA1c in cases in which HbA1c is measured by switching between plural measurement modes.

One aspect of the liquid chromatography measurement method of the present disclosure is a measurement method including: switching between a first measurement mode using a liquid chromatography method in which hemoglobin A1c and a hemoglobin variant are measured in a measurement sample by sequentially delivering a first component-separating eluent, a second component-separating eluent and a wash eluent to an analytical column, and a second measurement mode using the liquid chromatography method in which the hemoglobin A1c is measured by sequentially delivering the first component-separating eluent and the wash eluent to the analytical column; delivering the wash eluent in the first measurement mode prior to an influence from the second component-separating eluent disappearing such that a first retention time of the hemoglobin A1c in the first measurement mode and a second retention time of the hemoglobin A1c in the second measurement mode are substantially the same as each other; and delivering the first component-separating eluent after the wash eluent.

According to the above aspect of the present disclosure, measurement time may be shortened while suppressing offset from occurring in the retention time of HbA1c in cases in which HbA1c is measured by switching between plural measurement modes. Note that "substantially the same" in "substantially the same retention time" encompasses not only cases in which the two are completely the same, but also encompasses when there is a difference in the retention times as long as the difference is ±5% or less.

In aspect of the present disclosure, the delivery duration in the first measurement mode for delivering the first component-separating eluent after delivering the wash eluent may be longer than a delivery duration in the second measurement mode for delivering the first component-separating eluent after delivering the wash eluent.

The aspect of the present disclosure may further include: preparing a holding unit capable of holding at least two measurement's worth of measurement sample or more, in which two measurement's worth of one calibrator of a low concentration calibrator or a high concentration calibrator is held; performing calibration in the first measurement mode and the second measurement mode; preparing the holding unit in which two measurement's worth of the other calibrator of the low concentration calibrator or the high concentration calibrator is held; and performing calibration in the first measurement mode and the second measurement mode.

The second aspect of the present disclosure is a liquid chromatography measurement instrument including: a switching unit that is configured to switch between a first measurement mode using a liquid chromatography method in which hemoglobin A1c and a hemoglobin variant are measured in a measurement sample by sequentially delivering a first component-separating eluent, a second component-separating eluent and a wash eluent to an analytical column, and a second measurement mode using the liquid chromatography method in which the hemoglobin A1c is measured by sequentially delivering the first component-separating eluent and the wash eluent to the analytical column; a first delivery unit that is configured to deliver the wash eluent in the first measurement mode prior to an influence from the second component-separating eluent disappearing such that a first retention time of the hemoglobin A1c in the first measurement mode and a second retention time of the hemoglobin A1c in the second measurement mode are substantially the same as each other; and a second delivery unit that is configured to deliver the first component-separating eluent after the wash eluent.

According to the above aspect, measurement time may be shortened while suppressing offset from occurring in the retention time of HbA1c in cases in which HbA1c is measured by switching between plural measurement modes.

In the above aspect of the present disclosure, a delivery duration in the first measurement mode for delivering the first component-separating eluent after delivering the wash eluent may be longer than a delivery duration in the second measurement mode for delivering the first component-separating eluent after delivering the wash eluent.

The above aspect of the present disclosure may further include a pre-filter for filtering the measurement sample, the first component-separating eluent, the second component-separating eluent, and the wash eluent, the pre-filter being integrated with the analytical column.

According to the above aspect, for example, dead volume or line volume may be reduced at the pre-filter connection portion, enabling differences between instruments to be reduced. In cases in which switching between measurement modes is not performed, no particular issue arises from such differences existing between instruments; however, in instruments in which switching between measurement modes is performed, such differences between instruments have an effect on retention time offset. From the viewpoint of reducing retention time offset, there is therefore an advantage to integrating the pre-filter with the analytical column.

The third aspect of the present disclosure is a liquid chromatography measurement program that causes a computer to execute processing, the processing including: switching between a first measurement mode using a liquid chromatography method in which hemoglobin A1c and a hemoglobin variant are measured in a measurement sample by sequentially delivering a first component-separating eluent, a second component-separating eluent and a wash eluent to an analytical column, and a second measurement mode using the liquid chromatography method in which the hemoglobin A1c is measured by sequentially delivering the first component-separating eluent and the wash eluent to the analytical column; delivering the wash eluent in the first measurement mode prior to an influence from the second component-separating eluent disappearing such that a first retention time of the hemoglobin A1c in the first measurement mode and a second retention time of the hemoglobin A1c in the second measurement mode are substantially the same as each other; and delivering the first component-separating eluent after the wash eluent.

The fourth aspect of the present disclosure is a non-transitory storage medium storing a program that causes a computer to execute liquid chromatography measurement processing, the liquid chromatography measurement processing including: switching between a first measurement mode using a liquid chromatography method in which hemoglobin A1c and a hemoglobin variant are measured in a measurement sample by sequentially delivering a first component-separating eluent, a second component-separating eluent and a wash eluent to an analytical column, and a second measurement mode using the liquid chromatography method in which the hemoglobin A1c is measured by sequentially delivering the first component-separating eluent and the wash eluent to the analytical column; delivering the wash eluent in the first measurement mode prior to an influence from the second component-separating eluent disappearing such that a first retention time of the hemoglobin A1c in the first measurement mode and a second retention time of the hemoglobin A1c in the second measurement mode are substantially the same as each other; and delivering the first component-separating eluent after the wash eluent.

According to the above aspects, measurement time may be shortened while suppressing offset from occurring in the retention time of HbA1c in cases in which HbA1c is measured by switching between plural measurement modes.

The present disclosure thus enables measurement time to be shortened while suppressing offset from occurring in the retention time of HbA1c in cases in which HbA1c is measured by switching between plural measurement modes.

BRIEF DESCRIPTION OF THE DRAWINGS

Exemplary embodiments of the present disclosure will be described in detail based on the following figures, wherein.

DETAILED DESCRIPTION

Figure 1:
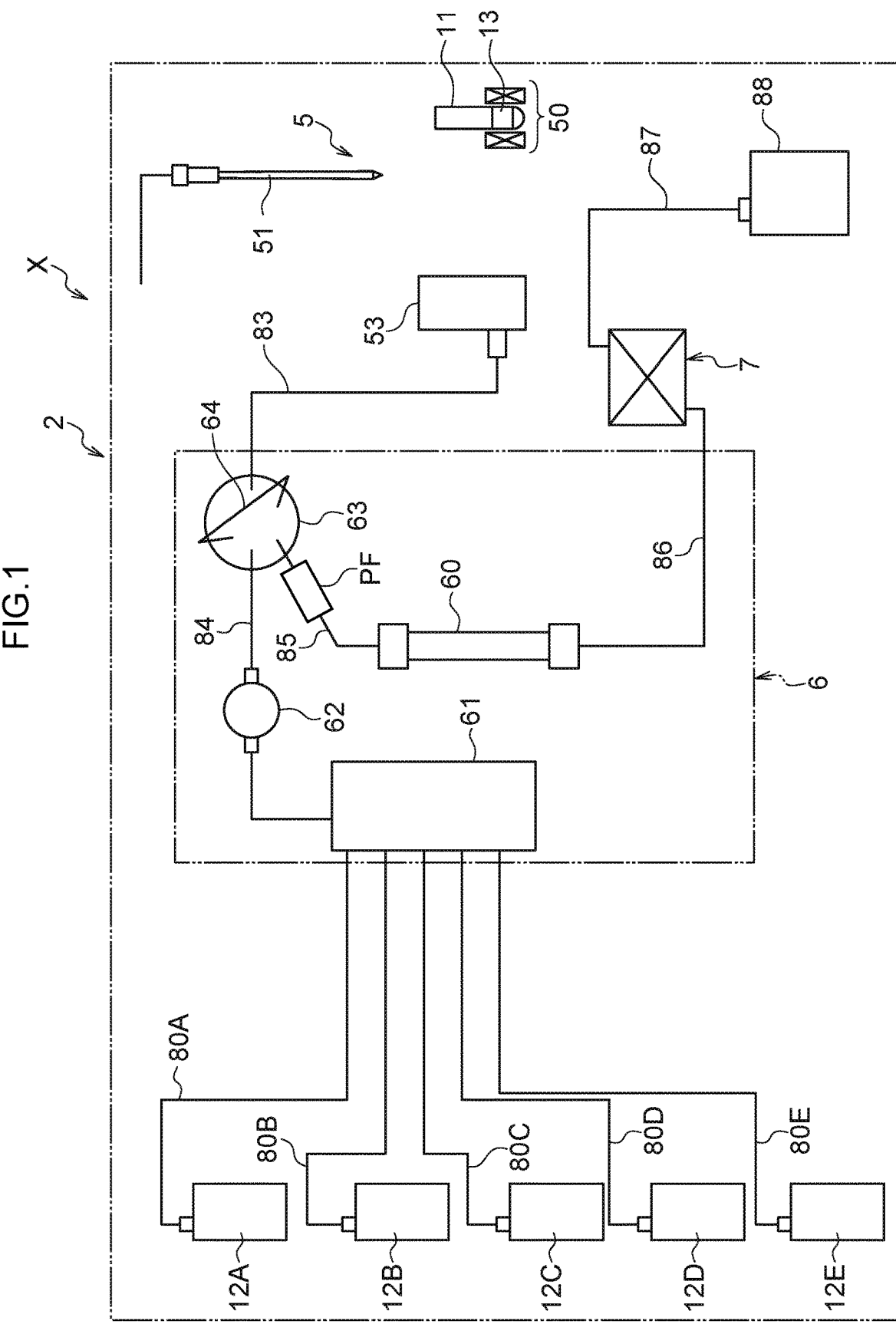
FIG. 1. is a schematic configuration diagram of an HPLC instrument.

FIG. 1 is a schematic configuration diagram illustrating a high performance liquid chromatography (HPLC) instrument X used in high performance liquid chromatography.

The HPLC instrument X is configured such that when set with a blood collection tube 11, the HPLC instrument X automatically measures the concentration of glycated hemoglobin (HbA1c) in whole blood. The HPLC instrument X is provided with an instrument body 2 including, for example, plural eluent bottles 12A, 12B, 12C, 12D, and 12E (five in FIG. 1).

Each eluent bottle 12A to 12E holds a respective eluent A to E to be supplied into an analytical column 60, described later. Each eluent has, for example, a different composition, component ratio, pH, osmotic pressure, and so on according to use.

The instrument body 2 includes a sample preparation unit 5, an analyzer unit 6, and a photometer unit 7.

The blood collection tubes 11 are, for example, housed in a rack (not illustrated in the drawings) and configured so as to move to a position enabling collection by a nozzle 51 of the sample preparation unit 5, described later.

The sample preparation unit 5 is a unit that prepares samples from blood taken from the blood collection tubes 11 for introducing into the analytical column 60. The sample preparation unit 5 includes the nozzle 51 and a dilution tank 53.

The nozzle 51 is for collecting of various solutions, such as a blood sample 13 of the blood collection tubes 11. The nozzle 51 is capable of drawing up or expelling a solution, and is movable in both a vertical direction and a horizontal direction. Operation of the nozzle 51 is controlled by a controller 100, described later.

The analyzer unit 6 controls adsorption/desorption of a biological component to a packing material of the analytical column 60, and provides various biological components to the photometer unit 7. The temperature setting of the analyzer unit 6 is set, for example, to approximately 40° C. The analytical column 60 holds a packing material for selective adsorption of the hemoglobin in the sample. A copolymer of methacrylic acid and an ester of methacrylic acid is, for example, employed as the packing material.

In addition to the analytical column 60, the analyzer unit 6 also includes a manifold 61, a fluid delivery pump 62, and an injection valve 63.

The manifold 61 is for selectively supplying an eluent from a specific eluent bottle of the plural eluent bottles 12A to 12E to the analytical column 60. The manifold 61 is connected to the eluent bottles 12A, 12B, 12C, 12D, and 12E through respective lines 80A to 80E, and the manifold 61 is connected to the injection valve 63 through line 84.

The fluid delivery pump 62 is for imparting motive force to move the eluents through the injection valve 63 and is provided partway along the line 84.

The injection valve 63 is for collecting a fixed amount of sample for introduction and configured so as to be capable of introducing the introduction sample into the analytical column 60. The injection valve 63 includes plural introduction ports and discharge ports (not illustrated in the drawings). An injection loop 64 is connected to the injection valve 63. The injection loop 64 is configured so as to be capable of holding a fixed amount (for example, several μL) of solution. Switching the injection valve 63 as appropriate enables selection of: a state in which the injection loop 64 is in communication with the dilution tank 53, and the introduction sample is supplied from the dilution tank 53 to the injection loop 64; and a state in which the injection loop 64 is in communication with the analytical column 60 through a pre-filter PF and a line 85, and the introduction sample is introduced from the injection loop 64 to the analytical column 60. A six-way valve, for example, may be employed as such an injection valve 63. The pre-filter PF is a filter for filtering samples and eluents.

The photometer unit 7 is for optically detecting hemoglobin contained in the solution desorbed from the analytical column 60, and is connected through a line 87 to a liquid waste tank 88 to discharge the desorption solution from the analytical column 60.

Figure 2:
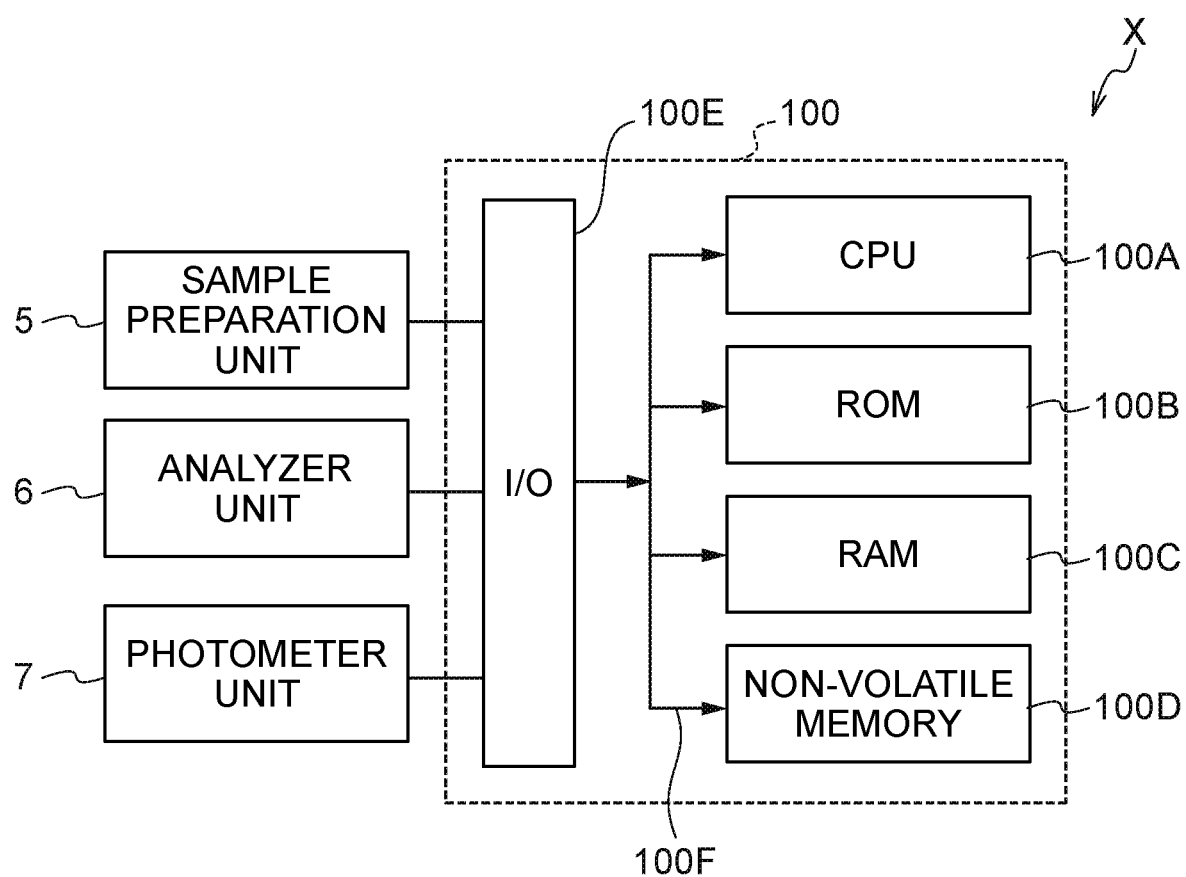
FIG. 2 is a configuration diagram of a control system of an HPLC instrument.

FIG. 2 illustrates a block diagram of a control system of the HPLC instrument X. As illustrated in FIG. 2, the HPLC instrument X includes the controller 100. The controller 100 is configured by a central processing unit (CPU) 100A that is a processor, read only memory (ROM) 100B, random access memory (RAM) 100C, non-volatile memory 100D, and an input/output interface (I/O) 100E respectively connected together through a bus 100F. Further, the HPLC instrument X includes an operation section (not illustrated in the drawings) for receiving input from an operator.

The sample preparation unit 5, the analyzer unit 6, and the photometer unit 7 are connected to the I/O 100E.

As an example, in the present exemplary embodiment, a liquid chromatography measurement program, described later, is pre-stored in the non-volatile memory 100D. The CPU 100A reads and executes the liquid chromatography measurement program stored in the non-volatile memory 100D. The liquid chromatography measurement program may be stored on a storage medium such as a CD-ROM and executed by being read using a CD-ROM drive or the like.

Explanation follows regarding operation of the present exemplary embodiment.

Figure 3:
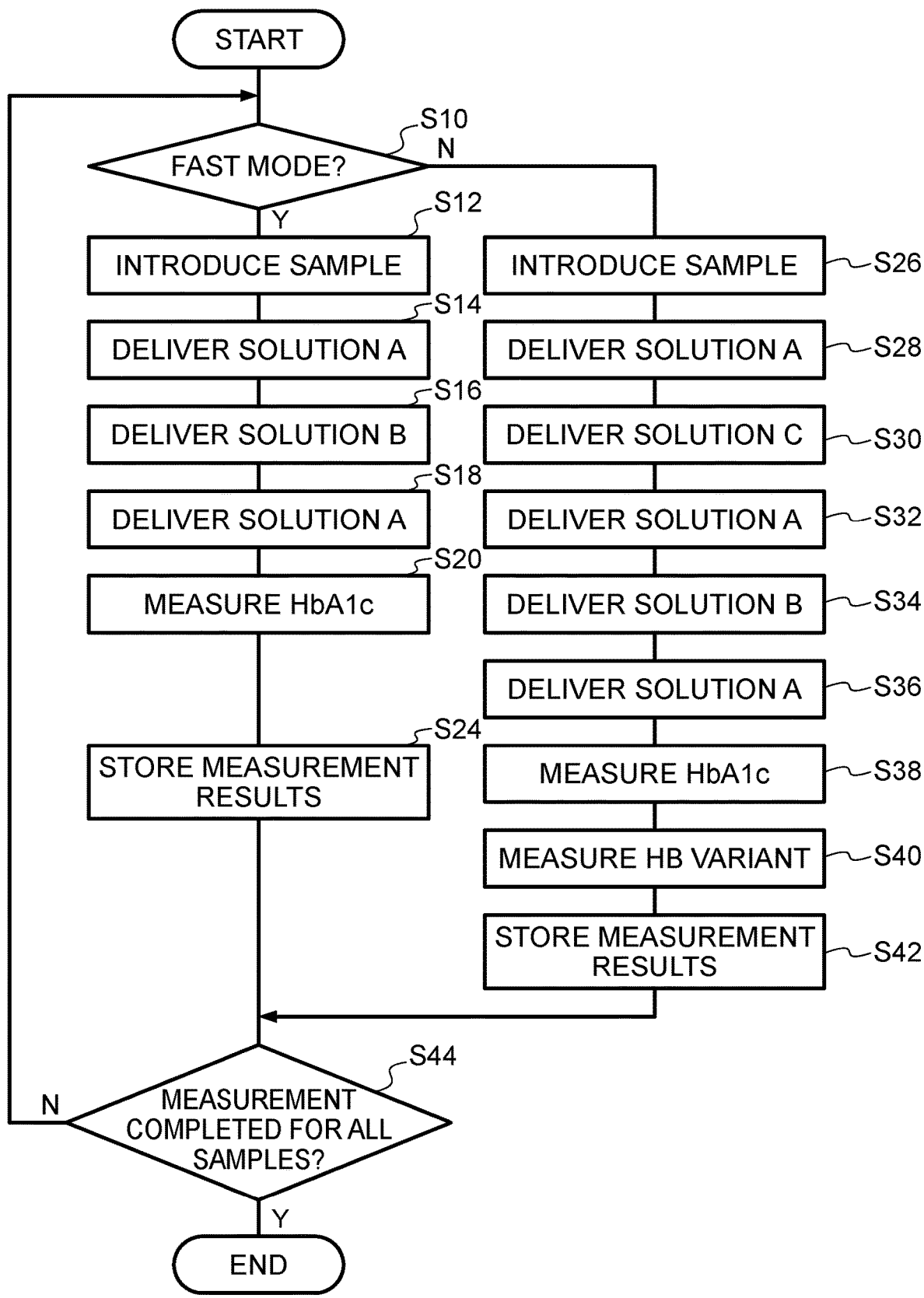
FIG. 3 is a flowchart of liquid chromatography measurement program.

FIG. 3 illustrates a flowchart of liquid chromatography measurement processing executed by the CPU 100A of the controller 100.

First, the operator may set a blood collection tube 11 containing the blood sample 13. The blood collection tube 11 is transported to the collection position by moving the rack housing the plural blood collection tubes 11.

When an operator gives a measurement start instruction, the CPU 100A reads and executes the liquid chromatography measurement program stored in the non-volatile memory 100D.

At step S10, determination is made as to whether the blood sample 13 to be measured is to be measured in the variant mode or to be measured in the fast mode (also referred to as normal mode). Processing transitions to step S12 for the fast mode measurement, and processing transitions to step S26 for the variant mode measurement. Note that the variant mode (first measurement mode) is a measurement mode that uses a liquid chromatography method to measure HbA1c and hemoglobin variants in the blood sample 13 by successively delivering plural types of eluent, described later, to the analytical column 60 in a predetermined sequence. Further, the fast mode (second measurement mode) is a measurement mode that, among plural types of eluent, successively delivers a plural common eluents common to the eluents used in the variant mode to the analytical column 60 in a predetermined sequence, to measure HbA1c.

Whether to use the variant mode or the fast mode as the measurement mode for measuring each blood sample 13 is, for example, preset by a user. For example, the measurement mode may be identified and set by reading bar code information affixed to the blood collection tube 11, by receiving an instruction signal from a host computer, or by input from the operation section. This enables compatibility even in situations in which blood collection tubes 11 to be measured by the fast mode and by the variant mode are housed together in the rack.

The plural types of eluents of the present exemplary embodiment are solution A to solution C. Solution A (first component-separating eluent) is an eluent for eluting HbA1c and for equilibrating the analytical column 60. Solution B (wash eluent) is an eluent for eluting all hemoglobin that remains on the analytical column 60, namely, is eluent for washing the analytical column 60. Solution C (second component-separating eluent) is an eluent for eluting hemoglobin other than HbA1c after the HbA1c has been eluted. The order of hemoglobin elution strength, from the highest is: solution B, solution C, solution A.

In the variant mode, solution A, solution B, and solution C are delivered, in this predetermined sequence, to the analytical column 60, and measurement performed. In the fast mode, solution A and solution B are delivered, in this predetermined sequence, to the analytical column 60 and measurement performed. Namely, solution A and solution B are common eluents having common specifications in the variant mode and the fast mode, and solution C is a non-common eluent used solely in the variant mode.

At step S12, the blood sample 13 is introduced. Specifically, the blood sample 13 is first collected from the blood collection tube 11. Namely, the blood sample 13 is collected from the blood collection tube 11 by actuating the nozzle 51. The blood sample 13 collected by the nozzle 51 is supplied to the dilution tank 53 by actuating the nozzle 51.

Then, by switching the injection valve 63, the sample held in the injection loop 64 is filtered through the pre-filter PF and introduced to the analytical column 60. HbA1c, Hb variants, and the like are adsorbed onto the packing material when the sample is introduced into the analytical column 60.

At step S14, solution A is supplied to the analytical column 60 for a predetermined duration. HbA1c is thereby eluted from the analytical column 60.

At step S16, the solution B is supplied to the analytical column 60 for a predetermined duration. All hemoglobin that remained on the analytical column 60 is thereby eluted and the analytical column 60 is thereby washed.

At step S18, solution A is supplied to the analytical column 60 for a predetermined duration. The analytical column 60 is accordingly equilibrated.

In this manner, in the fast mode, the sequence of solutions delivered to the analytical column 60 is solution A→solution B→solution A.

The desorption solution discharged from the analytical column 60 and containing various types of hemoglobin is supplied to the photometer unit 7 through line 86. The desorption solution is guided to the liquid waste tank 88 through line 87.

The photometer unit 7 continuously illuminates light onto the desorption solution and outputs light reception results (light absorbance) therefrom to the controller 100. The controller 100 then calculates a chromatogram.

Figure 4:
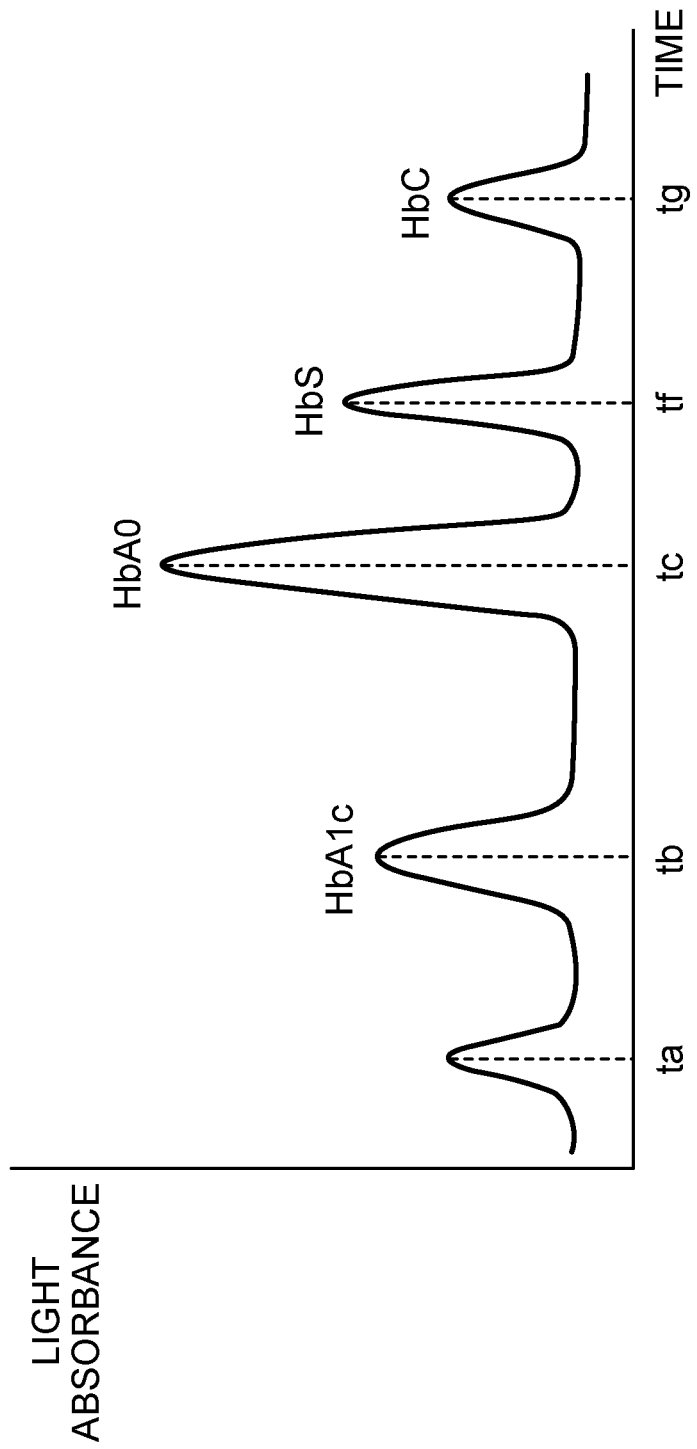
FIG. 4 is a graph illustrating an example of a chromatogram.

As illustrated in FIG. 4, a chromatogram is a graph illustrating a relationship between the time elapsed since the start of measurement and light absorbance as the light reception results. Which hemoglobin was detected may be found from which position the peak appeared at in the chromatogram, and the hemoglobin concentration may be found from the integrated value of light absorbance of the peaks (spike portions), namely, the magnitude of the area under the peaks.

In the present exemplary embodiment, for example, in cases in which the measurement sample includes HbA1c and HbA0, some other form of hemoglobin, and specific hemoglobin variants such as hemoglobin C and hemoglobin S, suppose, as illustrated in FIG. 4, that peaks are expected to appear at each time point ta, tb, tc, tf, and tg when eluents are switched over and delivered in sequence to the analytical column 60. In such cases, determination may be made as to whether or not some other form of hemoglobin was detected from the calculated chromatogram by determining whether or not a peak appears at time point ta seconds. Similarly, determination may be made as to whether or not HbA1c was detected by determining whether or not a peak appears at time point tb, determination may be made as to whether or not HbA0 was detected by determining whether or not a peak appears at time point tc, determination may be made as to whether or not HbS was detected by determining whether or not a peak appears at time point tf, and determination may be made as to whether or not variant hemoglobin C was detected by determining whether or not a peak appears at time point tg. Further, determination may be made that an unexpected type of hemoglobin was detected in cases in which a peak appeared at a time point other than at ta, tb, tc, tf, and tg. The concentration of each type of hemoglobin may be measured from the magnitude of light absorbance at the respective time point.

In the present exemplary embodiment, in the fast mode, for example, in cases in which the measurement sample includes HbA1c, HbA0, some other form of hemoglobin, hemoglobin C, and hemoglobin S, suppose, as illustrated in FIG. 4, that a peak for HbA1c is expected to appear at time point tb from the start of measurement when eluents are switched over in the above control sequence and delivered in sequence to the analytical column 60. In such cases, determination may be made as to whether or not HbA1c was detected by determining whether or not a peak appears in the vicinity of tb in the calculated chromatogram.

Accordingly, at step S20, HbA1c is measured based on the calculated chromatogram. Namely, as described above, determination is made as to whether or not a peak appears in the vicinity of tb, and determination is made that HbA1c was detected if a peak appears in the vicinity of tb. Then, the concentration of the HbA1c is measured from the integrated value of light absorbance of the peak in the vicinity of tb.

At step S24, the measurement results are stored in the non-volatile memory 100D. Namely, the concentration of HbA1c and whether or not hemoglobin variants were detected is stored in the non-volatile memory 100D.

At step S44, determination is made as to whether or not the above measurement has been completed for all of the blood collection tubes 11. In cases in which measurement has been completed for all of the blood collection tubes 11, the current routine is ended. In cases in which there is a blood collection tube 11 for which measurement has not been completed, processing returns to step S10 and determination is made as to whether the blood sample 13 to be measured is to be measured in the variant mode or measured in the fast mode.

Processing transitions to step S26 in cases in which determination at step S10 is that measurement is to be measurement in the variant mode.

At step S26, the blood sample 13 is introduced, similarly to at step S12.

At step S28, solution A is supplied to the analytical column 60 for a predetermined duration. HbA1c is thereby eluted from the analytical column 60.

At step S30, solution C is supplied to the analytical column 60 for a predetermined duration. Hemoglobin other than HbA1c is thereby eluted from the analytical column 60 after the HbA1c has been eluted.

At step S32, solution A is supplied to the analytical column 60 for a predetermined duration. The analytical column 60 is thereby equilibrated.

At step S34, solution B is supplied to the analytical column 60 for a predetermined duration. All hemoglobin that remained on the analytical column 60 is thereby eluted and the analytical column 60 washed.

At step S36, solution A is supplied to the analytical column 60 for a predetermined duration. The analytical column 60 is thereby equilibrated.

In this manner, in the variant mode, the sequence of solutions delivered to the analytical column 60 is solution A→solution C→solution A→solution B→solution A.

At step S38, HbA1c is measured, similarly to at step S20.

At step S40, hemoglobin variants are measured. Namely, as described above, determination is made as to whether or not a hemoglobin variant has been detected by determining whether or not a peak appears at a time point other than tb and tc. Then, in cases in which a peak appears at a time point other than tb and tc, the concentration of that hemoglobin variant is measured from the integrated value of the peak.

At step S42, the measurement result is stored in the non-volatile memory 100D. Namely, the concentration of the HbA1c and the concentration of the hemoglobin variant are stored in the non-volatile memory 100D.

By adopting such an approach, the present exemplary embodiment is able to switch measuring between the fast mode and the variant mode using a single instrument.

Figure 5:
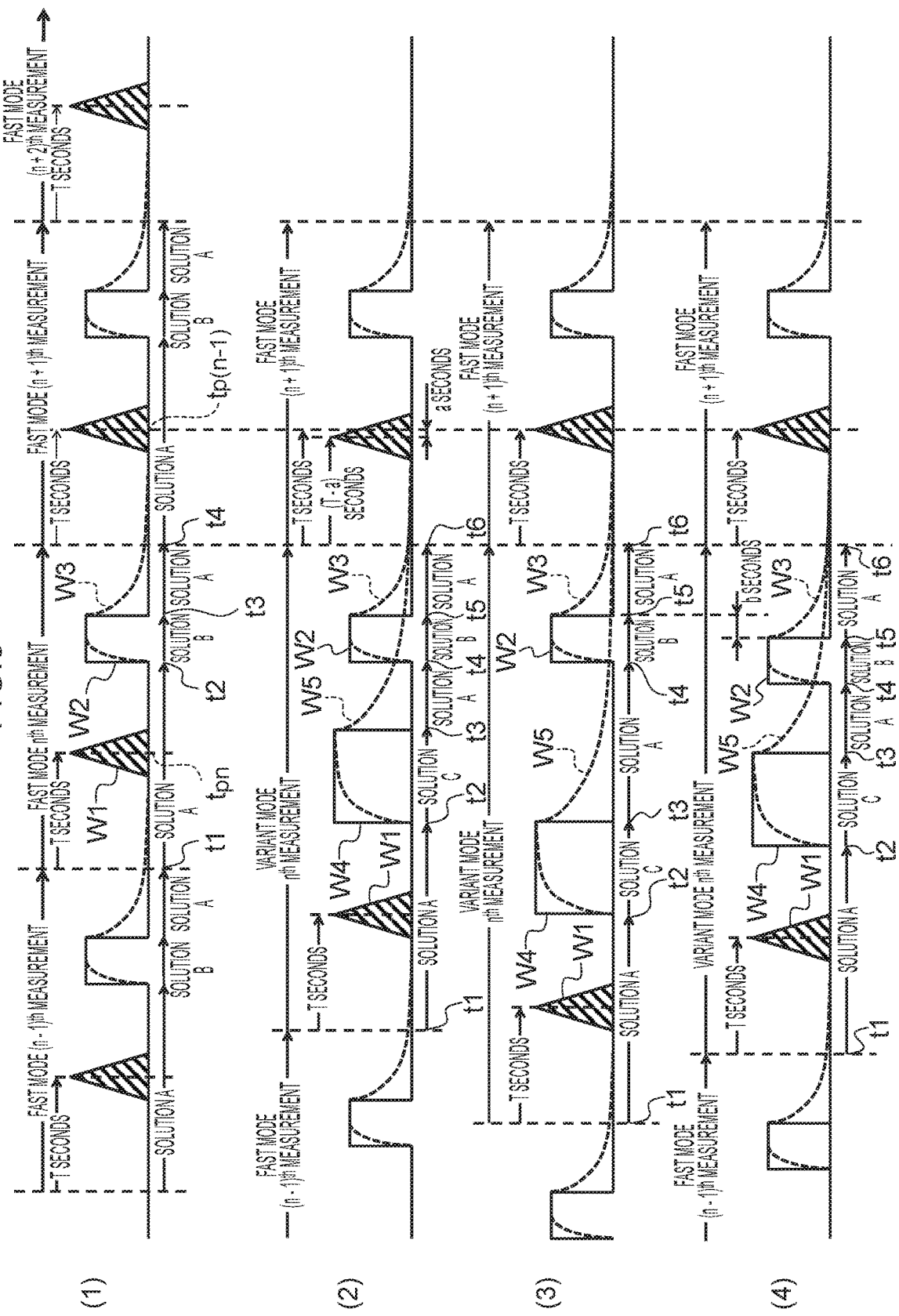
FIG. 5 illustrates diagrams for explaining delivery timings of respective eluents in the measurements, in which (1) is a diagram for explaining delivery timings of respective eluents for successive fast mode measurements, (2) is a diagram for explaining delivery timings of respective eluents when measurement is switched from a variant mode to a fast mode, (3) is a diagram for explaining a case of lengthened delivery duration for a solution A delivered after a solution C in a variant mode, and (4) is a diagram for explaining a case of lengthened delivery duration for a solution A delivered after a solution B in a variant mode.

Next, with reference to (1) of FIG. 5, explanation follows regarding the delivery timing of solution A and solution B, the timing at which the peak for HbA1c appears, and the amount of solution B remaining in the analytical column 60 after solution B has been delivered to the analytical column 60 in cases in which successive measurements are taken in the fast mode.

In (1) of FIG. 5, a waveform W1 illustrated by hatching represents a waveform of the light absorbance peak for HbA1c. A waveform W2 represents the delivery timing of solution B. A waveform W3 indicates the amount of solution B remaining in the analytical column 60. Namely, the vertical axis in (1) of FIG. 5 has two meanings: the light absorbance of HbA1c and the amount of solution B remaining.

As illustrated in (1) of FIG. 5, for example, for the $n^{th}$ measurement in the fast mode, solution A is delivered from time point t1 to time point t2, solution B is delivered from time point t2 to time point t3, and solution A is delivered from time point t3 to time point t4. In cases in which solution B is delivered from time point t2 to time point t3, the amount (concentration) of solution B remaining in the analytical column 60 is not like waveform W2, and is actually a waveform that gradually increases and then gradually decreases like that of waveform W3 due to solution B mixing with the solution A that is already inside the line for introduction into the analytical column 60. The peak for HbA1c appears at time point $t_{pn}$. The duration T in seconds from time point t1, this being the measurement start time, to time point $t_{pn}$ at which the peak for HbA1c appears is referred to as the retention time.

Delivery of solution A for the $(n+1)^{th}$ measurement starts from time point t4, i.e. delivery of solution A for the $(n+1)^{th}$ measurement starts even though a state exists in which a small amount of the solution B that was delivered at the $n^{th}$ measurement remains in the analytical column 60. This approach shortens the duration of one measurement by as much as possible, and, so long as the next $(n+2)^{th}$ measurement will also be a fast mode measurement, the amount of solution B remaining in the analytical column 60 at the start time of the next $(n+2)^{th}$ measurement is substantially the same as the amount of solution B remaining in the analytical column 60 at the start time of the $(n+1)^{th}$ measurement. Thus, for cases of successive fast mode measurements, the amounts of solution B remaining at the measurement start times are substantially the same. The retention time at the $(n+1)^{th}$ measurement, namely, the duration from time point t1 to time point $t_{pn}$, and the retention time of the $(n+1)^{th}$ measurement, namely, the duration from time point t4 to time point $t_{p(n-1)}$, for example, are accordingly substantially the same as each other, and no particular issues arise.

Next, for cases in which the variant mode is switched to the fast mode, explanation follows regarding the delivery timing of solution A to solution C, the timing at which the peak for HbA1c appears, the amount of solution C remaining in the analytical column 60 after the solution C has been delivered to the analytical column 60, and the amount of solution B remaining in the analytical column 60 after the solution B has been delivered to the analytical column 60.

As illustrated in (2) of FIG. 5, for example, for the $n^{th}$ measurement in the variant mode, solution A is delivered from time point t1 to time point t2, solution C is delivered from time point t2 to time point t3, solution A is delivered from time point t3 to time point t4, solution B is delivered from time point t4 to time point t5, and solution A is delivered from time point t5 to time point t6. Note that time points t4 to t6 in (2) of FIG. 5 correspond with the respective time points t2 to t4 in (1) of FIG. 5. Namely, the delivery duration of solution B in (2) of FIG. 5 (duration from t4 to t5) is substantially the same as the delivery duration of solution B in (1) of FIG. 5 (duration from t2 to t3), and the delivery duration of solution A in (2) of FIG. 5 (duration from t5 to t6) is substantially the same as the delivery duration of solution A in (1) of FIG. 5 (duration from t3 to t4).

Note that waveform W4 represents a delivery timing for solution C. Waveform W5 indicates the amount of solution C remaining in the analytical column 60. In cases in which solution C is delivered from time point t2 to time point t3, the amount of solution C remaining in the analytical column 60 is not like in waveform W4, and is actually a waveform that gradually increases and then gradually decreases like that of waveform W5, similarly to the case of solution B described above. At time point t6 at which the $(n+1)^{th}$ measurement starts, a state accordingly arises in which a small amount of the solution C that was delivered at the $n^{th}$ measurement still remains in the analytical column 60. Further, this is also a state in which there is a small amount of solution B remaining, similarly to in (1) of FIG. 5.

As illustrated in (2) of FIG. 5, the timing at which the peak for HbA1c appears at the $(n+1)^{th}$ measurement is therefore a seconds earlier than in the case of (1) of FIG. 5, and the retention time is (T−a) seconds. This is because although at time point t6 the amount of solution B remaining is substantially the same as in the case of (1) of FIG. 5, there is solution C remaining.

Thus, as illustrated in (3) of FIG. 5, in the present exemplary embodiment, the delivery duration of the solution A delivered after solution C is made longer than in the case of (2) of FIG. 5. Namely, the delivery amount of the solution A delivered after solution C is made larger than in the case of (2) of FIG. 5. In the example in (3) of FIG. 5, the delivery duration of the solution A (duration from t3 to t4) delivered after the solution C is made longer than in the case of (2) of FIG. 5. Namely, the delivery duration is lengthened for delivering solution A at step S32. Note that the delivery duration of solution C, and of solution B and the solution A delivered after solution A are substantially the same as in the case of (2) of FIG. 5.

Thus, as illustrated in (3) of FIG. 5, at time point t6, at which the $(n+1)^{th}$ measurement starts, the solution C delivered at the $n^{th}$ measurement is no longer present, and so the influence from solution C has disappeared. Since the amount of remaining solution B is the same as in the case of (1) of FIG. 5, the retention time of HbA1c at the $(n+1)^{th}$ measurement is T seconds, which is substantially the same as the retention time of HbA1c for cases of successive fast mode measurements, as in (1) of FIG. 5. Note that the delivery duration of the solution A delivered after solution C is not necessarily set to the duration until the solution C no longer issues from the analytical column 60. It is sufficient to set the delivery duration of the solution A delivered after solution C to a duration such that as an offset in retention time does not occur, even when a small amount of solution C remains in the analytical column 60.

As illustrated in (4) of FIG. 5, configuration may be made such that the delivery duration of solution A delivered after the solution B is b seconds longer than in the case of (2) of FIG. 5, instead of making the delivery duration of the solution A delivered after solution C longer. Namely, the delivery duration of the solution A delivered at step S36 may be lengthened. The measurement duration at the $n^{th}$ measurement (the duration from t1 to t6) may thereby be shortened compared to the case of (3) of FIG. 5. This is because the amount of solution B remaining is reduced commensurate to the increased amount of solution C remaining.

Thus, in the present exemplary embodiment, in cases in which HbA1c is measured in the variant mode, the delivery duration is controlled for at least one of the solution A delivered to the analytical column 60 after delivery of solution C, namely, the solution A delivered directly after the solution C, or the solution A delivered directly after solution B, such that the retention time of HbA1c is substantially the same as the retention time of HbA1c measured in the fast mode. Accordingly, remaining components of solution B and solution C that affect the elution of HbA1c, as well as the influence from their remaining amounts, may be set so as to be substantially the same at the measurement start time in the fast mode and in the variant mode. Thus, when switching between the variant mode and the fast mode and measuring HbA1c, an offset may be suppressed from occurring in the retention time of HbA1c.

Note that in the present exemplary embodiment, as one mode of controlling elution conditions inside the analytical column 60, explanation has been given of a case in which the delivery durations of eluents are controlled such that the retention times of HbA1c measured in the variant mode and the fast mode are substantially the same as each other. However, the mode of controlling the elution conditions inside the analytical column 60 is not limited thereto. For example, other modes of controlling elution conditions inside the analytical column 60 include controlling an elution delivery timing, controlling an elution delivery amount, controlling an elution flow rate, adding a purging solution, and changing the elution concentration. Such elution conditions may be made different to the elution conditions in cases in which there is no switching between the variant mode and the fast mode so as to control such that the retention time of HbA1c is substantially the same when measured in the variant mode and the fast mode.

In cases in which the first retention time measured in the variant mode and the second retention time measured in the fast mode are different, the delivery timing of solution B in the variant mode may be made different according to the difference between the first retention time and the second retention time.

Generally, due to there being more types of eluent used in the variant mode than in the fast mode, the influence from the solution C remains in the next measurement, and so normally the retention time of HbA1c is shifted earlier in the next measurement. Since solution B is used in both the variant mode and the fast mode, it is thought that there is no influence therefrom on the difference in retention times, and that it is the difference in the amount of solution C remaining that influences the difference in retention time.

Figure 6:
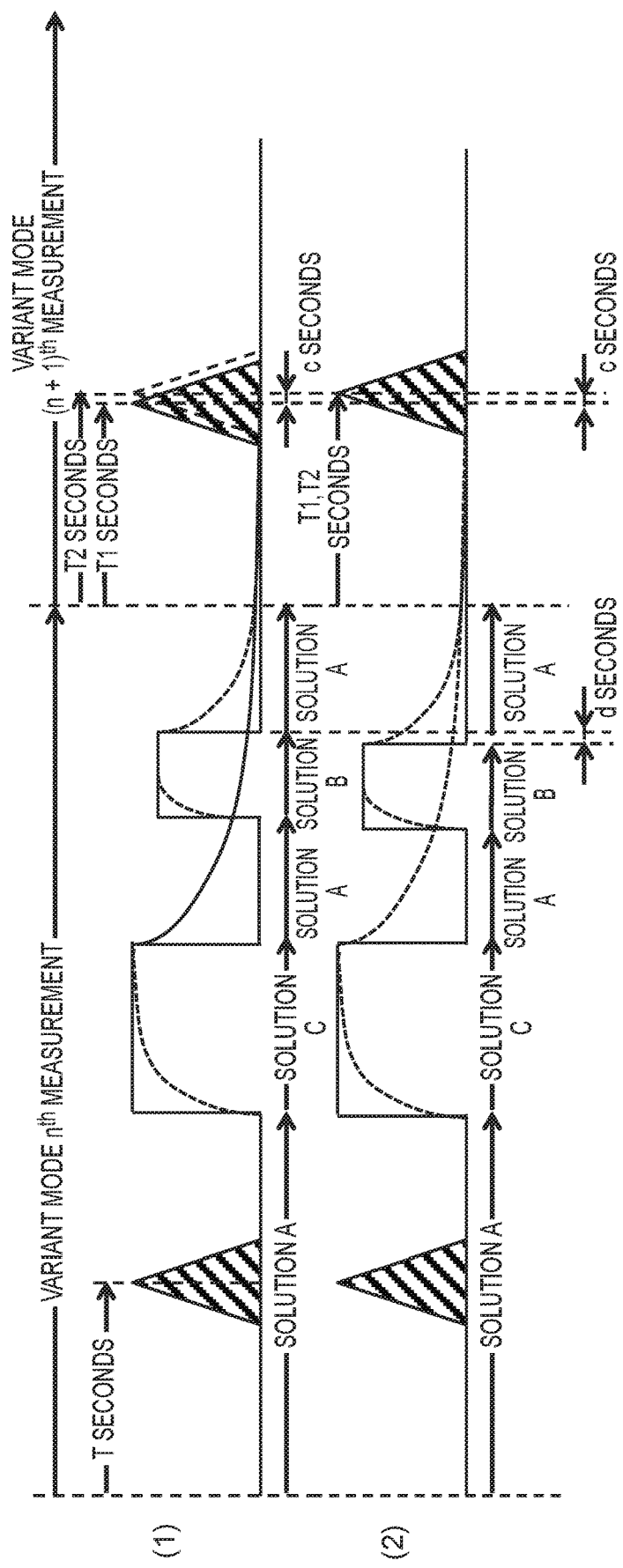
FIG. 6 illustrates diagrams (1) for explaining a case in which feedback control is not performed based on retention time offset, and (2) for explaining a case in which feedback control is performed based on a retention time offset.

Accordingly, as illustrated in (2) of FIG. 6, for example, feedback control is performed to make the delivery timing for solution B d seconds earlier according to the difference (c seconds) between the first retention time and the second retention time. Thus, the composite remaining amount of solution C and solution B at the $n^{th}$ measurement is adjusted, and as illustrated in (2) of FIG. 6, the first retention time of T1 seconds measured next in the variant mode is substantially the same as the second retention time of T2 seconds measured in the fast mode. Note that in the example in (2) of FIG. 6, since the first retention time measured in the variant mode is c seconds shorter than the second retention time measured in the fast mode, the delivery timing for solution B is made earlier by d seconds. However, for example, were the first retention time measured in the variant mode to be c seconds later than the second retention time measured in the fast mode, the delivery timing for solution B would be delayed by d seconds. The extent of adjustment in the delivery timing for solution B according to the difference between the first retention time and the second retention time, namely, a correspondence relationship between c seconds and d seconds, may be found by experimentation in advance or may be found from the measurement results from repeating actual measurements.

Note that although the feedback control above is performed, for example, when the remaining amount of solution C influences retention time during measurement in the variant mode, there is no limitation thereto.

Figure 7:
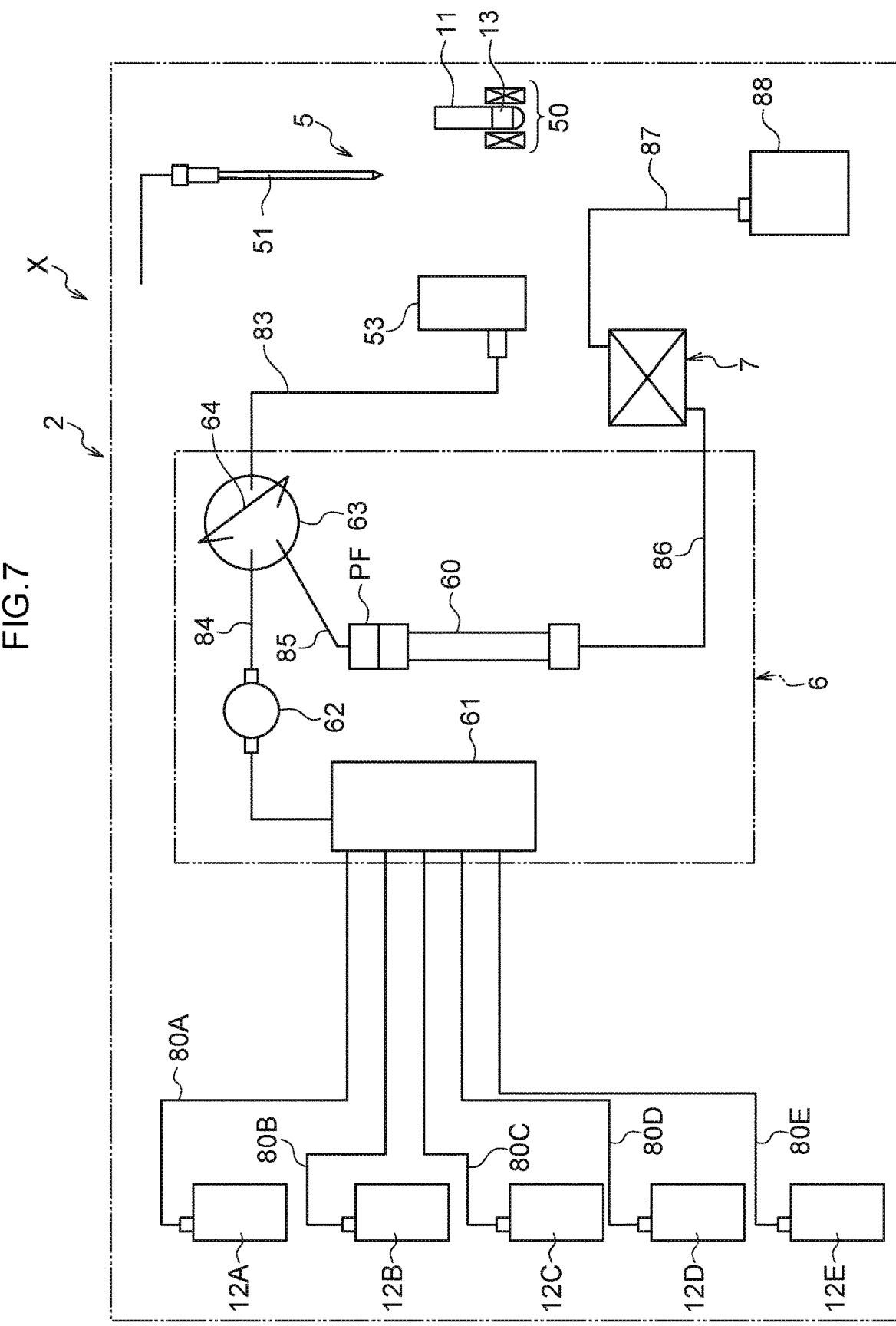
FIG. 7 is schematic configuration diagram illustrating a modified example of an HPLC instrument.

Further, in the present exemplary embodiment, although explanation has been given regarding a case in which the pre-filter PF is provided between the injection valve 63 and the analytical column 60, there is no limitation thereto. For example, as illustrated in FIG. 7, configuration may be made in which the pre-filter PF is integrated with the analytical column 60. This enables the volume of line 85 to be reduced and enables the amount of solution C remaining to be suppressed as much as possible. The occurrence of offset in HbA1c retention time may be therefore suppressed as much as possible.

In a liquid chromatography instrument, in cases in which there is concern that the measurement conditions might have changed, such as when changing out analytical columns or when maintenance is performed on the liquid chromatography instrument, normally a calibration sample (referred to as a calibrator below) is used to calibrate the liquid chromatography instrument (referred to as calibration below). Further, even in cases in which there is no concern that the measurement conditions have changed, calibration is normally performed regularly to maintain measurement accuracy.

When doing so, two types of calibrator are prepared, these being a low concentration LOW calibrator and a high concentration HIGH calibrator, and calibration needs to be performed with each calibrator.

In cases in which there is switching between the variant mode and the fast mode in a single liquid chromatography instrument as in the present exemplary embodiment, calibration needs to be performed in each of the measurement modes. However, for example, when calibration is performed using the LOW calibrator and the HIGH calibrator in the variant mode, and then a switch made to the fast mode where calibration is then performed using low concentration and high concentration calibrators, this results in cumbersome washing of the instrument and preparation of calibrators. There is accordingly an increased possibility of user error, such as putting in the wrong sequence or putting in the wrong number of calibrators. Namely, in case of the example above, if measurement is performed in the sequence: LOW (variant mode)→HIGH (variant mode)→LOW (fast mode) →HIGH (fast mode), then the calibrator must be switched three times, and the flow path must be washed out three times. Further, the LOW calibrator and the HIGH calibrator must be prepared for each measurement mode, i.e. for the variant mode and for the fast mode.

To address this issue, a line 83 laid to connect the dilution tank 53 and the injection valve 63 together may be given a volume capable of holding at least two measurement's worth of measurement sample, and the following approach adopted. For example, two measurement's worth of LOW calibrator may be held in the line 83 and calibration performed using the LOW calibrator in each measurement mode, i.e. in the variant mode and the fast mode, recording the measurement results of the respective measurement modes. Two measurement's worth of HIGH calibrator may then be held in the line 83 and calibration performed using the HIGH calibrator in each measurement mode, i.e. in the variant mode and the fast mode, recording the measurement results of the respective measurement modes.

Measurements are thereby performed in the sequence LOW (variant mode)→LOW (fast mode)→HIGH (variant mode)→HIGH (fast mode), with the calibrator switched once, and the flow path washed once. This enables calibration procedures to be simplified and enables costs to be reduced while also enabling a reduction in the possibility of user error, such as putting in the wrong sequence or putting in the wrong number of calibrators. Note that this method is not limited to application in calibration and may be employed in measurement (control measurement) using quality control solutions (samples), thereby enabling a contribution to cost reduction, such as a reduction in the amount of reagents used, a reduction in the amount of quality control solution used, and so on, and also enabling a reduction in user error, such as putting the quality control solutions in wrongly.

Further, in cases in which the line 83 having a volume capable of holding at least two measurement's worth of measurement sample is laid, a procedure may be adopted in which half of the measurement sample is used first to perform measurement in the fast mode, and when an abnormality has occurred, such as, as for example, when the measured value for HbA1c is an abnormally low value, the remaining half of the measurement sample is then used to perform measurement in the variant mode.

The present disclosure is not limited to the exemplary embodiment described above, and various modifications thereto are possible. For example, there is no limitation to an HPLC instrument for measuring hemoglobin concentration in blood, and the present disclosure may be applied to cases in which a sample other than blood is used, to cases in which concentration of a component other than hemoglobin concentration is measured, or to a liquid chromatography instrument other than an HPLC instrument.

What is claimed is:

1. A liquid chromatography measurement method, comprising:
   measuring, by liquid chromatography, a concentration of hemoglobin A1c and a hemoglobin variant in a first measurement sample that has been introduced to an analytical column using a first measurement mode in which the hemoglobin A1c and the hemoglobin variant are eluted from the analytical column by separately delivering a first component-separating eluent, a second component-separating eluent and a wash eluent to the analytical column, and
   after measuring the concentration of the hemoglobin A1c and the hemoglobin variant in the first measurement sample, measuring, by liquid chromatography, a concentration of hemoglobin A1c in a second measurement sample that has been introduced to the analytical column by switching to a second measurement mode in which the hemoglobin A1c in the second measurement sample is eluted from the analytical column by separately delivering only the first component-separating eluent and the wash eluent to the analytical column;
   wherein the wash eluent in the first measurement mode is delivered to the analytical column prior to removal of all of the second component-separating eluent eluted in the first measurement mode from the column such that a first retention time of the hemoglobin A1c in the first measurement mode and a second retention time of the hemoglobin A1c in the second measurement mode are substantially the same as each other; and
   the first component-separating eluent is delivered to the analytical column after the wash eluent in both the first measurement mode and the second measurement mode.

2. The liquid chromatography measurement method of claim 1, wherein a delivery duration in the first measurement mode for delivering the first component-separating eluent after delivering the wash eluent is longer than a delivery duration in the second measurement mode for delivering the first component-separating eluent after delivering the wash eluent.

3. The liquid chromatography measurement method of claim 1, further comprising:
   preparing a holding unit capable of holding at least two measurement's worth of measurement sample or more, in which two measurement's worth of one calibrator of a low concentration calibrator or a high concentration calibrator is held;
   performing calibration in the first measurement mode and the second measurement mode;
   preparing the holding unit in which two measurement's worth of the other calibrator of the low concentration calibrator or the high concentration calibrator is held; and performing calibration in the first measurement mode and the second measurement mode.

4. A liquid chromatography measurement instrument comprising:
   a controller that is configured to measure, by liquid chromatography, a concentration of hemoglobin A1c and a hemoglobin variant in a first measurement sample that has been introduced to an analytical column using a first measurement mode in which the hemoglobin A1c and the hemoglobin variant are eluted from the analytical column by separately delivering a first component-separating eluent, a second component-separating eluent and a wash eluent to the analytical column, and
   after measuring the concentration of the hemoglobin A1c and the hemoglobin variant in the first measurement sample, the controller is configured to measure, by liquid chromatography, a concentration of hemoglobin A1c in a second measurement sample that has been introduced to the analytical column by switching to a second measurement mode in which the hemoglobin A1c in the second measurement sample is eluted from the analytical column by separately delivering only the first component-separating eluent and the wash eluent to the analytical column;
   a first delivery unit that is configured to deliver the wash eluent in the first measurement mode prior to removal of all of the second component-separating eluent eluted in the first measurement mode from the column such that a first retention time of the hemoglobin A1c in the first measurement mode and a second retention time of the hemoglobin A1c in the second measurement mode are substantially the same as each other; and
   a second delivery unit that is configured to deliver the first component-separating eluent to the analytical column after the wash eluent in both the first measurement mode and the second measurement mode.

5. The liquid chromatography measurement instrument of claim 4, wherein a delivery duration in the first measurement mode for delivering the first component-separating eluent after delivering the wash eluent is longer than a delivery duration in the second measurement mode for delivering the first component-separating eluent after delivering the wash eluent.

6. The liquid chromatography measurement instrument of claim 4, further comprising a pre-filter for filtering the measurement sample, the first component-separating eluent, the second component-separating eluent, and the wash eluent, the pre-filter being integrated with the analytical column.

7. A non-transitory storage medium storing a program that causes a computer to execute liquid chromatography measurement processing, the liquid chromatography measurement processing comprising:
   measuring, by liquid chromatography, a concentration of hemoglobin A1c and a hemoglobin variant in a first measurement sample that has been introduced to an analytical column using a first measurement mode in which the hemoglobin A1c and the hemoglobin variant are eluted from the analytical column by separately delivering a first component-separating eluent, a second component-separating eluent and a wash eluent to the analytical column, and
   after measuring the concentration of the hemoglobin A1c and the hemoglobin variant in the first measurement sample, measuring, by liquid chromatography, a concentration of hemoglobin A1c in a second measurement sample that has been introduced to the analytical column by switching to a second measurement mode in which the hemoglobin A1c in the second measurement sample is eluted from the analytical column by separately delivering only the first component-separating eluent and the wash eluent to the analytical column;
   wherein the wash eluent in the first measurement mode is delivered to the analytical column prior to removal of all of the second component-separating eluent eluted in the first measurement mode from the column such that a first retention time of the hemoglobin A1c in the first measurement mode and a second retention time of the hemoglobin A1c in the second measurement mode are substantially the same as each other; and
   the first component-separating eluent is delivered to the analytical column after the wash eluent in both the first measurement mode and the second measurement mode.

* * * * *